United States Patent
Huang

(10) Patent No.: US 11,682,484 B2
(45) Date of Patent: Jun. 20, 2023

(54) AUTOMATED ANALYSIS OF OCT RETINAL SCANS

(71) Applicant: MERIT CRO, INC., Madison, WI (US)

(72) Inventor: Yijun Huang, Fitchburg, WI (US)

(73) Assignee: MERIT CRO, INC., Madison, WI (US)

( * ) Notice: Subject to any disclaimer, the term of this patent is extended or adjusted under 35 U.S.C. 154(b) by 0 days.

(21) Appl. No.: 17/850,441

(22) Filed: Jun. 27, 2022

(65) Prior Publication Data

US 2022/0344035 A1 Oct. 27, 2022

Related U.S. Application Data

(63) Continuation of application No. 16/612,827, filed as application No. PCT/US2018/032211 on May 11, 2018, now Pat. No. 11,373,749.

(60) Provisional application No. 62/505,393, filed on May 12, 2017.

(51) Int. Cl.
| | |
|---|---|
| A61B 3/10 | (2006.01) |
| A61B 5/00 | (2006.01) |
| G06T 7/00 | (2017.01) |
| G16H 30/40 | (2018.01) |
| G06T 7/10 | (2017.01) |
| G06N 20/00 | (2019.01) |

(52) U.S. Cl.
CPC .............. *G16H 30/40* (2018.01); *A61B 3/102* (2013.01); *A61B 5/004* (2013.01); *A61B 5/0066* (2013.01); *A61B 5/4842* (2013.01); *A61B 5/4848* (2013.01); *G06N 20/00* (2019.01); *G06T 7/0012* (2013.01); *G06T 7/10* (2017.01); *G06T 2207/10101* (2013.01); *G06T 2207/20081* (2013.01); *G06T 2207/20216* (2013.01); *G06T 2207/30041* (2013.01)

(58) Field of Classification Search
CPC ........ G16H 30/40; A61B 3/102; A61B 5/004; A61B 5/0066; A61B 5/4842; A61B 5/4848; G06N 20/00; G06T 7/0012; G06T 7/10; G06T 2207/10101; G06T 2207/20081; G06T 2207/20216; G06T 2207/30041
See application file for complete search history.

(56) References Cited

U.S. PATENT DOCUMENTS

| | | | | |
|---|---|---|---|---|
| 2011/0141259 | A1* | 6/2011 | Nakano | A61B 3/0025 348/78 |
| 2012/0184845 | A1* | 7/2012 | Ishikawa | A61B 3/102 600/425 |
| 2012/0274898 | A1* | 11/2012 | Sadda | G01B 9/02091 351/246 |
| 2016/0174830 | A1* | 6/2016 | Rubin | A61B 3/102 351/246 |
| 2016/0183783 | A1* | 6/2016 | Sadda | G01B 9/02083 351/206 |
| 2017/0119247 | A1* | 5/2017 | Walsh | A61B 3/102 |

* cited by examiner

*Primary Examiner* — Molly Wilburn
(74) *Attorney, Agent, or Firm* — Casimir Jones S.C.; J. Mitchell Jones

(57) ABSTRACT

The present invention is related to improved methods for analysis of images of the vitreous and/or retina and/or choroid obtained by optical coherence tomography and to methods for making diagnoses of retinal disease based on the reflectivity profiles of various vitreous and/or retinal and/or choroidal layers of the retina.

15 Claims, 3 Drawing Sheets

AUTOMATED ANALYSIS OF OCT RETINAL SCANS

CROSS REFERENCE TO RELATED APPLICATIONS

This application is a continuation of U.S. application Ser. No. 16/612,827, filed Nov. 12, 2019, now allowed, which is a 371 U.S. National Phase Entry of International Application No. PCT/US2018/032211, filed May 11, 2018, which claims the benefit U.S. Provisional Patent Application No. 62/505,393, filed May 12, 2017, each of which is incorporated herein by reference in its entirety.

FIELD OF THE INVENTION

The present invention is related to improved methods for analysis of images of the retina obtained by optical coherence tomography and to methods for making diagnoses of retinal disease based on the reflectivity profiles of various retinal layers of the retina. The present invention can be extended to optical coherence tomography application in other medical and non-medical fields, including but not limited to, OCT imaging of other eye related tissues and structures (cornea, tear film, anterior segment, etc.), dental tissues, the gastrointestinal tract, the cardiovascular wall, the respiratory wall, and monitoring biointegration of implanted biomaterials.

BACKGROUND OF THE INVENTION

Vision starts in the retina located at the posterior part of the eye. "Rete", the Latin origin of its name standing for "net", connotes with two important properties, a two-dimensional layer structure and a multitude of connections. The retina is composed of several heavily interconnected neuronal layers, each with a specific functional property from the light reception to signal processing and data reduction.

In contrast to the rather similar principal organization of the retina in layers, its topography varies substantially between mammalian species, presumably due to evolutionary influences of the environmental conditions. In humans and non-human primates (NHPs), a central region of high visual acuity, the macula with an associated fovea, has evolved and is located temporal to the optic nerve head. In carnivores (e.g. dog, cat) a region of increased visual acuity with a higher cone and ganglion cell density is located temporal to the optic nerve and is referred to as an area centralis but lacks a fovea. Many non-predator species (e.g. sheep, cow, horse, pig) possess a less clearly defined region of relatively increased acuity termed the visual streak that typically extends horizontally across the retina, both temporal and nasal to the optic nerve. This configuration is believed to follow the basic visual needs of each species, namely high-acuity vision of the horizon, low-sensitivity vision of the (bright) sky, and high-sensitivity vision of the (relatively dim) ground.

Traditionally, fundus photography and fluorescein angiography have been used to assess macroscopic retinal structure and its changes in disease, with fine details of retinal and choroidal architecture being accessible only via ex vivo processes like histology and immunohistochemistry. It was a major breakthrough in ophthalmic diagnostics when Optical Coherence Tomography (OCT) was first introduced as a novel tool for in vivo visualization of retinal layers. The resolution of third generation models of OCT equipment that became available a few years later finally turned out to be sufficient for experimental research and clinical practice to follow the course of disease and/or monitor the effects of a therapeutic intervention over time in individual eyes.

Recent literature suggests that, although reproducible OCT findings can be predictably obtained from healthy individuals, variable results can occur when retinal pathology is present due to the differences in acquisition and boundary identification between machines. See, e.g., Sadda S R, Wu Z, Walsh A C, Richine L, Dougall J, Cortez R, LaBree L D. Errors in retinal thickness measurements obtained by optical coherence tomography. Ophthalmology. 2006 Feb. 28; 113(2):285-93. Sadda S R, Joeres S, Wu Z, Updike P, Romano P, Collins A T, Walsh A C. Error correction and quantitative subanalysis of optical coherence tomography data using computer-assisted grading. Investigative ophthalmology & visual science. 2007 Feb. 1; 48(2): 839-48. Terasaki H, Shirasawa M, Yamashita T, et al. Comparison of foveal microstructure imaging with different spectral domain optical coherence tomography machines. Ophthalmology. 2012; 119(11):2319-27; Branchini L, Regatieri C V, Flores-Moreno I, et al. Reproducibility of choroidal thickness measurements across three spectral domain optical coherence tomography systems. Ophthalmology. 2012; 119(1):119-23; Bressler S B, Edwards A R, Chalam K V, et al. Reproducibility of spectral-domain optical coherence tomography retinal thickness measurements and conversion to equivalent time-domain metrics in diabetic macular edema. JAMA Ophthalmol. 2014; 132(9): 1113-22; and Suzuma K, Yamada Y, Liu M, et al. Comparing central retinal thickness in diabetic macular edema measured by two different spectral-domain optical coherence tomography devices. Japanese Journal of Ophthalmology. 2011; 55(6):620-4.

Along with variability in retinal presentations, clinicians can encounter ambiguous findings of non-glaucomatous optic neuropathies and normal optic nerve anatomy, which can lead to false positive and false negative OCT results.

Accordingly, what is needed in the art are improved systems and processes for analyzing OCT data sets.

SUMMARY OF THE INVENTION

The present invention is related to improved methods for analysis of images of the retina obtained by optical coherence tomography and to methods for making diagnoses of retinal disease based on the reflectivity profiles of various retinal layers of the retina.

In some embodiments, the present invention provides an optical coherence tomography (OCT) image analysis process comprising: visualizing an OCT image from a scan of a patients retina on a display device, wherein the image displays a plurality of retinal layers of the retina; indicating a portion of an edge of at least one of the vitreous and/or retinal and/or choroidal layers with a user input device to provide a designated retinal layer portion; via a computer processor, calculating a subject's retinal layer reflectivity profile for the designated retinal layer by a) averaging the pixel intensity in image columns for an area from about 10 to 50 pixels above and below the designated retinal layer portion to provide a local reflectivity profile and b) calculating the best fit of the local reflectivity profile against each column of the OCT image to identify the pixel location of the designated retinal layer across the PCT image; and graphically identifying the retinal layer on the OCT image on the display device.

In some embodiments, the best fit is calculated by a cross correlation algorithm. In some embodiments, the graphically identifying the retinal layer on the OCT image on the display device comprises overlaying a surface of the retinal layer with a computer generated line. In some embodiments, the processes further comprise identifying one or more lesions in the retinal layer with the user input device. In some embodiments, the processes further comprise associating the reflectivity profile with a disease state of the retina. In some embodiments, the processes further comprise the step of tagging the patient reflectivity profile with an information identification tag, wherein the information identification tag comprises information selected from the group consisting of name of the surface, location at the retina, disease indication and lesion indication. In some embodiments, the display device is networked with an SD-OCT device. In some embodiments, the processes further comprise the step of utilizing the SD-OCT device to obtain the OCT dataset of the scan of the patient's retina.

In some embodiments, the processes further comprise transmitting the tagged patient reflectivity profile and/or OCT image to a cloud server, wherein the cloud server comprises a plurality of OCT datasets from normal and diseased retinas; and via a processor associated with the remote server, applying one or more machine learning algorithms to analyze the patient reflectivity profile in relation to the plurality of OCT datasets from normal and diseased retinas to generate one or more algorithms a automatically segment retinal layers in an OCT image and/or associate a disease with an automated segmentation result. In some embodiments, the algorithm facilitates displaying a refined trace of the designated retinal layer. In some embodiments, the processes further comprise the step of displaying an image with a refined trace of the designated retinal layer generated by the algorithm. In some embodiments, the processes further comprise the step of transmitting the image with a refined trace of the designated retinal layer to a user.

In some embodiments, the processes further comprise the algorithm associates the reflectivity profile of the designated retinal layer with a disease state of the retina wherein the disease state is selected from the group consisting of subject's participating in clinical examinations and/or clinical trials. In some embodiments, the processes further comprise the step of using the algorithm to associate a disease state or normal state with the subject's retina. In some embodiments, the processes further comprise transmitting information about the disease state or normal state of the patient retina to a user. In some embodiments, the processes further comprise obtaining multiple patient retinal images over a defined time period for a given patient, via a processor automatically analyzing the multiple retinal images to identify changes in the retinal images, and displaying an image showing the identified changes in the patient retinal images.

In some embodiments, the one or more machine learning algorithms are selected from the group exemplified by but not limited to a neural network, a decision tree, a regression model, a k-nearest neighbor model, a partial least squares model, a support vector machine and an ensemble of the models that are integrated to define a algorithm.

In some embodiments, the present invention provides an optical coherence tomography (OCT) image analysis process comprising: visualizing an OCT dataset from a scan of a patients retina on a display device, wherein the image displays a plurality of cross-sectional retinal layers of the retina; indicating a portion of an edge of at least one of the retinal layers with a user input device to provide a designated retinal layer; at a user work station, calculating a patient reflectivity profile for the designated retinal layer and using the reflectivity profile to identify potential retinal locations of the designated retinal layer across the entire image; transmitting the patient reflectivity profile to a server remote from the user work station, wherein the remote server comprises a plurality of OCT datasets from normal and diseased retinas; via a processor associated with the remote server, applying one or more machine learning algorithms to analyze the patient reflectivity profile in relation to the plurality of OCT datasets from normal and diseased retinas to generate one or more algorithms a automatically segment retinal layers in an OCT image, automatically identify lesions in one or more retinal layers, and/or associate a disease with an automated segmentation or lesion identification result.

In some embodiments, the algorithm facilitates displaying a refined trace of the designated retinal layer. In some embodiments, the processes further comprise the step of displaying an image with a refined trace of the designated retinal layer generated by the algorithm. In some embodiments, the processes further comprise the step of transmitting the image with a refined trace of the designated retinal layer to a user.

In some embodiments, the algorithm associates the reflectivity profile of the designated retinal layer with a disease state of the retina wherein the disease state is selected from the group consisting of Age-related macular degeneration, diabetic retinopathy, retinitis pigmentosa, uveitis, central vein occlusion, and other retinal degenerations. In some embodiments, the processes further comprise the step of using the algorithm to associate a disease state or normal state with the patient retina. In some embodiments, the processes further comprise the algorithm identifies lesions in one or more retinal layers. In some embodiments, the type and/or location of the lesion is used to diagnose a disease or the retina and/or designate a stage of severity of a disease of the retina.

In some embodiments, the processes further comprise transmitting information about the disease state or normal state of the patient retina to a user. In some embodiments, the processes further comprise transmitting information about the lesion, disease associated with the lesion, or stage of severity of retinal disease to a user. In some embodiments, the processes further comprise the step of tagging the patient reflectivity profile with an information identification tag, wherein the information identification tag comprises information selected from the group consisting of name of the surface, location at the retina, disease indication and lesion indication, retinal location relating to known retinal landmark (e.g., fovea), age, gender, race, and animal species (other than human).

In some embodiments, the display device is networked with an SD-OCT device. In some embodiments, the processes further comprise the step of utilizing the SD-OCT device to obtain the OCT dataset of the scan of the patient's retina. In some embodiments, the server remote from the user work station is a cloud based server. In some embodiments, the processes further comprise the one or more machine learning algorithms are selected from the group exemplified by but not limited to a neural network, a decision tree, a regression model, a k-nearest neighbor model, a partial least squares model, a support vector machine and a an ensemble of the models that are integrated to define a algorithm.

In some embodiments, the processes further comprise obtaining multiple patient retinal images over a defined time period for a given patient, via a processor automatically analyzing the multiple retinal images to identify changes in the retinal images, and displaying an image showing the identified changes in the patient retinal images.

In some embodiments, the present invention provides an optical coherence tomography (OCT) image analysis process comprising: at a work station, visualizing an OCT dataset from a scan of a patients retina on a display device, wherein the image displays a plurality of cross-sectional retinal layers of the retina; via a processor associated with the work station, calculating patient reflectivity profiles for retinal layers and using the reflectivity profile to identify potential retinal locations of the designated retinal layer across the entire image; via the processor, applying one or more algorithms to automatically segment retinal layers in an OCT image, automatically identify lesions in one or more retinal layers, and/or associate a disease with an automated segmentation or lesion identification result, wherein the one or more algorithms are updated from a remote server performing machine learning algorithms on a database of OCT images for normal and diseased retinas; and displaying an output selected from the group consisting of an image of the patient retina with computer-generated traces defining one or more layers in the image of the patient retina, an association of a disease state with the reflectivity profiles associated with one or more retinal layers in the patient retina, an identification of lesions in one or more retinal layers, an image of one or more lesions in one or more retinal layers, an identification of disease of the retina associated with one or more lesions in one or more retinal layers, a designation of a stage of severity of a disease of the retina based on one or more identified lesions in one or more retinal layers, and combinations thereof.

In some embodiments, the algorithm associates the reflectivity profile of the designated retinal layer with a disease state of the retina wherein the disease state is selected from the group consisting of Age-related macular degeneration, diabetic retinopathy, retinitis pigmentosa, uveitis, central vein occlusion, and other retinal degenerations. In some embodiments, the processes further comprise the step of using the algorithm to associate a disease state or normal state with the patient retina. In some embodiments, the algorithm identifies lesions in one or more retinal layers. In some embodiments, the processes further comprise the type and/or location of the lesion is used to diagnose a disease or the retina and/or designate a stage of severity of a disease of the retina.

In some embodiments, the processes further comprise obtaining multiple patient retinal images over a defined time period for a given patient, via a processor automatically analyzing the multiple retinal images to identify changes in the retinal images, and displaying an image showing the identified changes in the patient retinal images. In some embodiments, the multiple patient retinal images are analyzed to monitor disease progression over time. In some embodiments, the multiple patient retinal images are analyzed to monitor response to a therapeutic agent over time. In some embodiments, the therapeutic agent is selected from the group consisting of a small molecule drug, a biologic drug, a nucleic acid, and a cell. In some embodiments, the therapeutic agent is delivered to the patient by a method selected from the group consisting of topical application to the surface of the eye, subconjunctival injection, systemically (IV, oral, subcutaneous, intramuscular), electrophoresis, intravitreal injection, subretinal delivery, and suprachoroidal delivery. In some embodiments, the therapeutic agent is soluble, insoluble in a suspension, of incorporated into a biomaterial platform.

In some embodiments, the work station is networked with an SD-OCT device. In some embodiments, the processes further comprise the step of utilizing the SD-OCT device to obtain the OCT dataset of the scan of the patient's retina. In some embodiments, the server remote from the work station is a cloud based server.

In some embodiments, the present invention provides an optical coherence tomography (OCT) image analysis process comprising: scanning the retina of a patient with an SD-OCT device to provide a patient OCT dataset; transmitting the patient OCT dataset to a server remote from the SC-OCT device, wherein the remote server comprises a processor configured to analyze the patient OCT dataset by one or more algorithms generated by machine learning algorithms trained with a plurality of OCT datasets from normal and diseased retinas, wherein the plurality of datasets comprise reflectivity profiles for retinal layers within the normal and diseased retinas; via a processor associated with the remote server, applying the one or more algorithms to identify retinal layers and/or lesions in the patient retina by their associated reflectivity profiles; and generating an output selected from the group consisting of an image of the patient retina with computer-generated traces defining one or more layers in the image of the patient retina, an association of a disease state with the reflectivity profiles associated with one or more retinal layers in the patient retina, an identification of lesions in one or more retinal layers, an image of one or more lesions in one or more retinal layers, an identification of disease of the retina associated with one or more lesions in one or more retinal layers, a designation of a stage of severity of a disease of the retina based on one or more identified lesions in one or more retinal layers, and combinations thereof.

In some embodiments, the processes further comprise transmitting the output selected from the group consisting of an image of the patient retina with computer-generated traces defining one or more layers in the image of the patient retina, association of a disease state with the reflectivity profiles associated with one or more retinal layers in the patient retina and combinations thereof to a user. In some embodiments, the processes further comprise the step of using the patient OCT dataset to further train the machine learning algorithm.

In some embodiments, the processes further comprise obtaining multiple patient retinal images over a defined time period for a given patient, via a processor automatically analyzing the multiple retinal images to identify changes in the retinal images, and displaying an image showing the identified changes in the patient retinal images. In some embodiments, the multiple patient retinal images are analyzed to monitor disease progression over time. In some embodiments, the multiple patient retinal images are analyzed to monitor response to a therapeutic agent over time. In some embodiments, the therapeutic agent is selected from the group consisting of a small molecule drug, a biologic drug, a nucleic acid, and a cell. In some embodiments, the therapeutic agent is delivered to the patient by a method selected from the group consisting of topical application to the surface of the eye, subconjunctival injection, systemically (IV, oral, subcutaneous, intramuscular), electrophoresis, intravitreal injection, subretinal delivery, and suprachoroidal delivery. In some embodiments, the therapeutic agent is soluble, insoluble in a suspension, of incorporated into a biomaterial platform.

In some embodiments, the present invention provides a process comprising: receiving a patient OCT dataset at a sever remote from an SD-OCT device, wherein the remote server comprises a processor configured to analyze the patient OCT dataset by one or more algorithms generated by machine learning algorithms trained with a plurality of OCT datasets from normal and diseased retinas, wherein the plurality of datasets comprise reflectivity profiles for retinal layers within the normal and diseased retinas; via a processor associated with the remote server, applying the one or more algorithms to identify retinal layers and or lesions in the patient retina by their associated reflectivity profiles; and generating an output selected from the group consisting of an image of the patient retina with computer-generated traces defining one or more layers in the image of the patient retina, association of a disease state with the reflectivity profiles associated with one or more retinal layers in the patient retina, an identification of lesions in one or more retinal layers, an image of one or more lesions in one or more retinal layers, an identification of disease of the retina associated with one or more lesions in one or more retinal layers, a designation of a stage of severity of a disease of the retina based on one or more identified lesions in one or more retinal layers, and combinations thereof.

In some embodiments, the processes further comprise transmitting the output selected from the group consisting of an image of the patient retina with computer-generated traces defining one or more layers in the image of the patient retina, association of a disease state with the reflectivity profiles associated with one or more retinal layers in the patient retina and combinations thereof to a user. In some embodiments, the processes further comprise the step of using the patient OCT dataset to further train the machine learning algorithm. In some embodiments, the processes further comprise obtaining multiple patient retinal images over a defined time period for a given patient, via a processor automatically analyzing the multiple retinal images to identify changes in the retinal images, and displaying an image showing the identified changes in the patient retinal images. In some embodiments, the multiple patient retinal images are analyzed to monitor disease progression over time. In some embodiments, the multiple patient retinal images are analyzed to monitor response to a therapeutic agent over time. In some embodiments, the therapeutic agent is selected from the group consisting of a small molecule drug, a biologic drug, a nucleic acid, and a cell. In some embodiments, the therapeutic agent is delivered to the patient by a method selected from the group consisting of topical application to the surface of the eye, subconjunctival injection, systemically (IV, oral, subcutaneous, intramuscular), electrophoresis, intravitreal injection, subretinal delivery, and suprachoroidal delivery. In some embodiments, the therapeutic agent is soluble, insoluble in a suspension, of incorporated into a biomaterial platform.

In some embodiments, the present invention provides a workstation comprising: a display device configured to display a an OCT retinal image received from an SD-OCT device; a user input device configured to enable a user to indicate a portion of an edge of at least one the retinal layer on the displayed OCT retinal image; and a computer configured to: receive the indicated portion of an edge of at least one retinal layer on the displayed OCT retinal image; calculate a patient retinal layer reflectivity profile for the designated retinal layer by a) averaging the pixel intensity in image columns for an area from about 10 to 50 pixels above and below the designated retinal layer portion to provide a local reflectivity profile and b) calculating the best fit of the local reflectivity profile against each column of the OCT image to identify the pixel location of the designated retinal layer across the PCT image; and graphically identify the retinal layer on the OCT image on the display device.

In some embodiments, the present invention provides a workstation comprising: a display device configured to display a an OCT retinal image received from an SD-OCT device; a user input device configured to enable a user to indicate a portion of an edge of at least one the retinal layer on the displayed OCT retinal image; and a computer configured to: receive the indicated portion of an edge of at least one retinal layer on the displayed OCT retinal image; calculate a patient reflectivity profile for the designated retinal layer and using the reflectivity profile to identify potential retinal locations of the designated retinal layer across the entire image; transmit the patient reflectivity profile to a server remote from the user computer, wherein the remote server comprises a plurality of OCT datasets from normal and diseased retinas, wherein the remote server is configured to apply one or more machine learning algorithms to analyze the patient reflectivity profile in relation to the plurality of OCT datasets from normal and diseased retinas to generate one or more algorithms associated with the reflectivity profile for the designated retinal layer; and receive from the remote server an output selected from the group consisting of an image of the patient retina with computer-generated traces defining one or more layers in the image of the patient retina, association of a disease state with the reflectivity profiles associated with one or more retinal layers in the patient retina, an identification of lesions in one or more retinal layers, an image of one or more lesions in one or more retinal layers, an identification of disease of the retina associated with one or more lesions in one or more retinal layers, a designation of a stage of severity of a disease of the retina based on one or more identified lesions in one or more retinal layers, and combinations thereof.

In some embodiments, the present invention provides a workstation comprising: a display device configured to display an OCT retinal image received from an SD-OCT device; and a computer configured to: transmit the patient OCT dataset to a server remote from the SD-OCT device, wherein the remote server comprises a processor configured to analyze the patient OCT dataset by one or more algorithms generated by machine learning algorithms trained with a plurality of OCT datasets from normal and diseased retinas, wherein the plurality of datasets comprise reflectivity profiles for retinal layers within the normal and diseased retinas, and wherein via the processor one or more algorithms are applied to identify retinal layers in the patient retina by their associated reflectivity profiles and generate an output selected from the group consisting of an image of the patient retina with computer-generated traces defining one or more layers in the image of the patient retina, association of a disease state with the reflectivity profiles associated with one or more retinal layers in the patient retina and combinations thereof; and receive from the remote server an output selected from the group consisting of an image of the patient retina with computer-generated traces defining one or more layers in the image of the patient retina, association of a disease state with the reflectivity profiles associated with one or more retinal layers in the patient retina, an identification of lesions in one or more retinal layers, an image of one or more lesions in one or more retinal layers, an identification of disease of the retina associated with one or more lesions in one or more retinal layers, a designation of a stage of severity of a disease of the retina based on one or more identified lesions in one or more retinal layers, and combinations thereof.

In some embodiments, the present invention provides a workstation comprising: a display device configured to display an OCT retinal image received from an SD-OCT device; and a computer configured to: calculate patient reflectivity profiles for retinal layers and using the reflectivity profile to identify potential retinal locations of the designated retinal layer across the entire image; apply one or more algorithms to automatically segment retinal layers in an OCT image, automatically identify lesions in one or more retinal layers, and/or associate a disease with an automated segmentation or lesion identification result, wherein the one or more algorithms are updated from a remote server performing machine learning algorithms on a database of OCT images for normal and diseased retinas; and display on the display device an output selected from the group consisting of an image of the patient retina with computer-generated traces defining one or more layers in the image of the patient retina, an association of a disease state with the reflectivity profiles associated with one or more retinal layers in the patient retina, an identification of lesions in one or more retinal layers, an image of one or more lesions in one or more retinal layers, an identification of disease of the retina associated with one or more lesions in one or more retinal layers, a designation of a stage of severity of a disease of the retina based on one or more identified lesions in one or more retinal layers, and combinations thereof.

In some embodiments, the present invention provides a non-transitory computer readable medium comprising software or instructions which control a processor to perform the steps of any of the processes described above.

DESCRIPTION OF THE INVENTION

Figure 1:
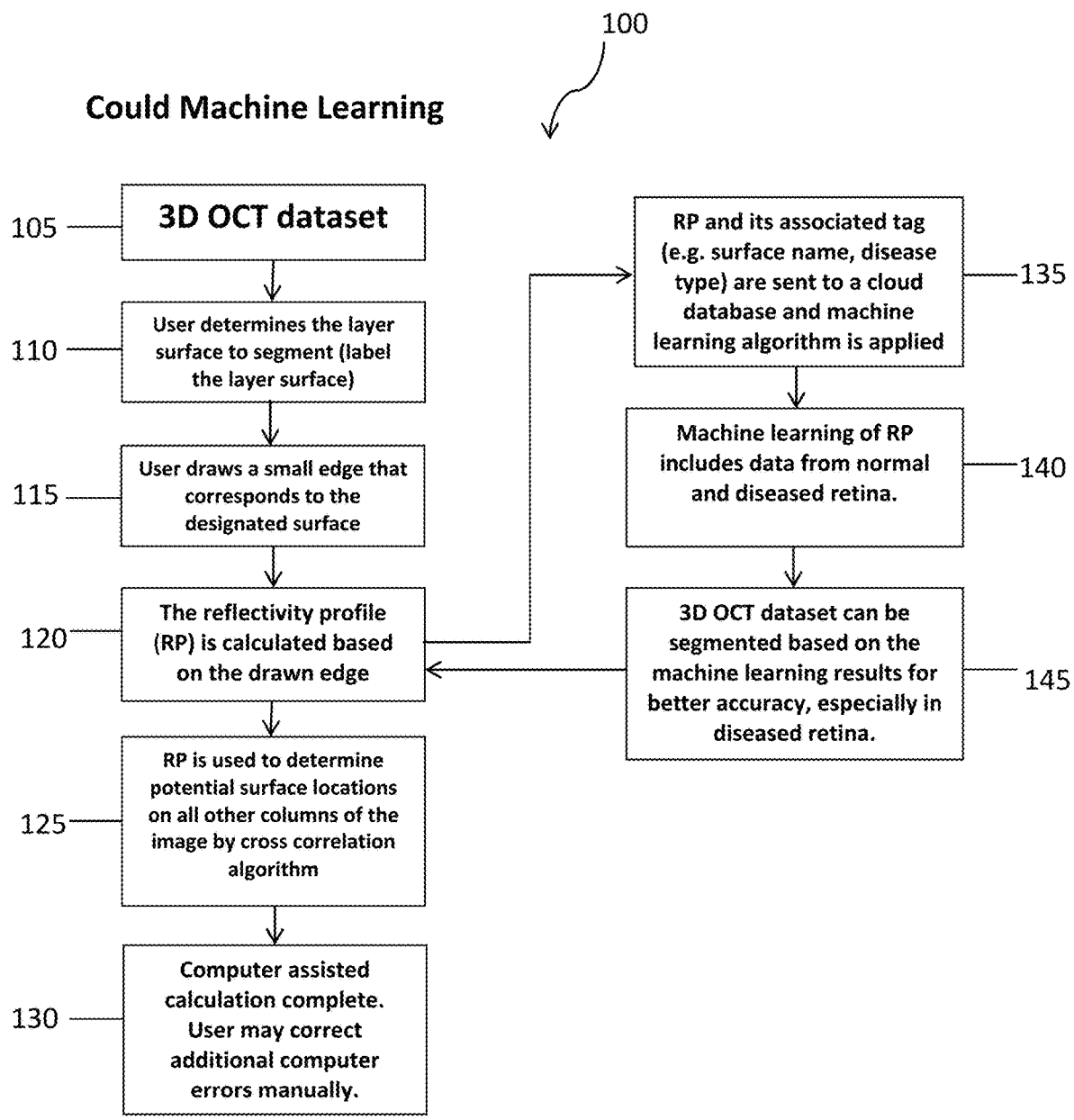
FIG. 1 is a process flow diagram of a process for automated segmentation of layers in an OCT image of a retina.

The present invention is related to improved methods for analysis of images of the retina and choroid obtained by optical coherence tomography (OCT) and to methods for making diagnoses of retinal disease based on the reflectivity profiles of various retinal layers of the retina. OCT provides cross-sectional images based on the reflective properties of the investigated sample. See, e.g., Fujimoto J G, Brezinski M E, Tearney G J, Boppart S A, Bouma B, et al. (1995) Optical biopsy and imaging using optical coherence tomography Nat Med. 1(9): p. 970-2. And Drexler W, Sattmann H, Hermann B, Ko T H, Stur M, et al. (2003) Enhanced visualization of macular pathology with the use of ultrahigh-resolution optical coherence tomography Arch Ophthalmol. 121(5): p. 695-706.

OCT is based on low-coherence interferometry using light with broad spectral bandwidth. Reflectance signal is detected when the combination of reflected light from the sample arm traveled the "same" optical distance ("same" meaning a difference of less than a coherence length) as the reflected light from the reference arm. In a layered tissue like retina, the amount of the reflected light in tissue is determined by the optical backscattering characteristics of the corresponding tissue layers, and consequently the alternating intensity in reflection (consisting of peaks and troughs) demonstrates the configuration of different tissue layers in the axial direction. (Huang Y, Cideciyan A V, Papastergiou G I, Banin E, Semple-Rowland S L, Milam A H, Jacobson S G. Relation of optical coherence tomography to microanatomy in normal and rd chickens. Investigative ophthalmology & visual science. 1998 Nov. 1; 39(12):2405-16.). A single measurement of the reflectivity versus depth at one specific location is called A-scan, whereas the composition of an image by alignment of several consecutive A-scans is called B-scan. See van Velthoven M E, Faber D J, Verbraak F D, van Leeuwen T G, de Smet M D (2007) Recent developments in optical coherence tomography for imaging the retina Prog Retin Eye Res. 26(1): p. 57-77.

A typical B-scan shows several, often alternating bands of low and high reflectivity, as plexiform layers of the retina have a higher level of reflectivity than nuclear layers [Jacobson S G, Cideciyan A V, Aleman T S, Pianta M J, Sumaroka A, et al. (2003) Crumbs homolog 1 (CRB1) mutations result in a thick human retina with abnormal lamination Hum Mol Genet. 12(9): p. 1073-8.]. However, these bands and the retinal layers associated with them vary in their extent with the topographical position in the retina, localized lesion alteration due to disease progression, and additionally species-dependent factors in retinal and choroidal architecture as mentioned above. So far, automated segmentation procedures were developed using several traditional image analysis approaches (e.g., Ishikawa H, Piette S, Liebmann J M, Ritch R. Detecting the inner and outer borders of the retinal nerve fiber layer using optical coherence tomography. Graefes Arch Clin Exp Ophthalmol. 2002; 240(5)362-371.). These segmentation techniques typically rely on the known retinal structure configuration in normal human retina. Consequently, segmentation errors are occur frequently seen in diseased retinas. Experimental quantifications based on A-scans have been performed in the past, but have not led to a widespread use of respective approaches See, e.g., Barthelmes D, Sutter F K, Kurz-Levin M M, Bosch M M, Helbig H, et al. (2006) Quantitative analysis of OCT characteristics in patients with achromatopsia and blue-cone monochromatism Invest Ophthalmol Vis Sci. 47(3): p. 1161-6; Barthelmes D, Gillies M C, Sutter F K (2008) Quantitative OCT analysis of idiopathic perifoveal telangiectasia Invest Ophthalmol Vis Sci. 49(5): p. 2156-62; Mataftsi A, Schorderet D F, Chachoua L, Boussalah M, Nouri M T, et al. (2007) Novel TULP1 mutation causing leber congenital amaurosis or early onset retinal degeneration Invest Ophthalmol Vis Sci. 48(11): p. 5160-7; Jacobson S G, Aleman T S, Cideciyan A V, Sumaroka A, Schwartz S B, et al. (2009) Leber congenital amaurosis caused by Lebercilin (LCAS) mutation: retained photoreceptors adjacent to retinal disorganization Mol Vis. 15: p. 1098-106.].

Accordingly, what is needed in the art are improved methods, systems and devices for automating the identification of retinal layers in the retina that can be visualized in an OCT retinal scan or image and/or for using information associated with the layers identified in an OCT retinal scan or image to make diagnoses or evaluations of the disease state of the retina and/or choroid and to allow lonitudtudinal monitoring of disease progression within an individual subject (animal or human).

Accordingly, in some embodiments, the processes and systems of the present invention utilize an OCT imaging system to obtain an OCT dataset or scan of a subject's retina. A number of OCT imaging systems are available that are suitable for imaging the fundus and/or retina of the eye. For example, clinicians currently have four prominent commercially available spectral-domain (SD) OCT models to choose from: Spectralis SD-OCT (Heidelberg Engineering), 3D OCT-2000 (Topcon Medical Systems), Avanti RTVue XR (Optovue), and Cirrus HD SD-OCT 5000 (Carl Zeiss Meditec). In some preferred embodiments, the SD-OCT imaging device captures between 26,000 and 70,000 axial-scans per second and provide 3D images and improved resolution, for example, an axial resolution of 3 μm to 6 μm within tissues. The increased speed and resolution provide an enhanced ability to visualize retinal layers. OCT's ability to define particular layers of the retina, known as "segmentation," as well as depth localization in tissue, also aids in identifying points of interest within the scans, such as lesions.

In some preferred embodiments, the OCT imaging device is communicably coupled to a workstation via a communications link. In various embodiments, the imaging device sends images to the workstation via the communications link. The communications link may be a network that communicably couples the imaging device to the workstation, or may be a bus that directly couples the imaging device to the workstation. The workstation may include any suitable type of computing system that is capable of processing and analyzing images according to the embodiments described herein.

In various embodiments, the workstation includes a real-time, interactive image analysis module. The real-time, interactive image analysis module may include any suitable types of software, firmware, and/or hardware that provide for the segmentation and quantification of images. Further, in some embodiments, the real-time, interactive image analysis module includes one or more non-transitory machine-readable storage media that provide for the segmentation and quantification of images.

The workstation also includes a display. The display may be a monitor, touch screen, or the like. Information relating to the segmentation and quantification of the images may be presented to a user of the workstation in real-time via the display. In addition, the user may interact with, or provide feedback to, the real-time, interactive image analysis module in order to direct the segmentation and quantification procedure. For example, the information that is displayed to the user may be updated in real-time as the user moves a pointer or cursor across the display.

In various embodiments, the user provides feedback to the real-time, interactive image analysis module through a user interface that is presented to the user via the display. The user interface may allow the user to control the segmentation and quantification procedure for an image by moving the pointer to positions on the display that correspond to specific locations on the image. In addition, the user interface may allow the user to adjust the information that is presented via the display. For example, the user may specify specific types of representations or specific measurements for the imaging subject represented by the image that are to be presented on the display.

In some embodiments, the workstation is configured to transmit images obtained by the OCT imaging device, and which may in some embodiments be annotated by segmentation, quantification or tagging by a user of the work station, via a network, such as a wired or wireless communications network, to a cloud based server at a location remote from the workstation. The function of the cloud based server is described in more detail below.

Figure 2:
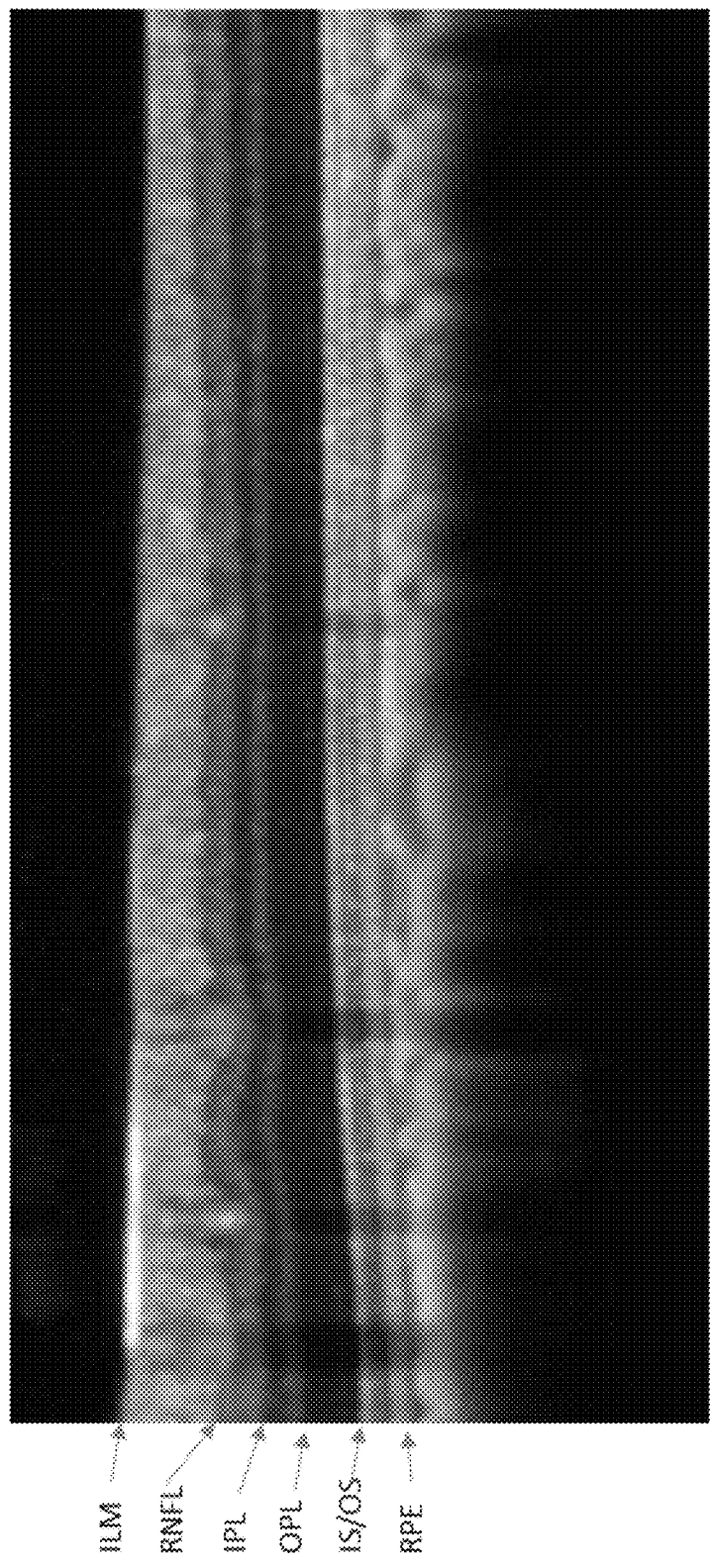
FIG. 2 is an OCT image of a retina.
Figure 3:
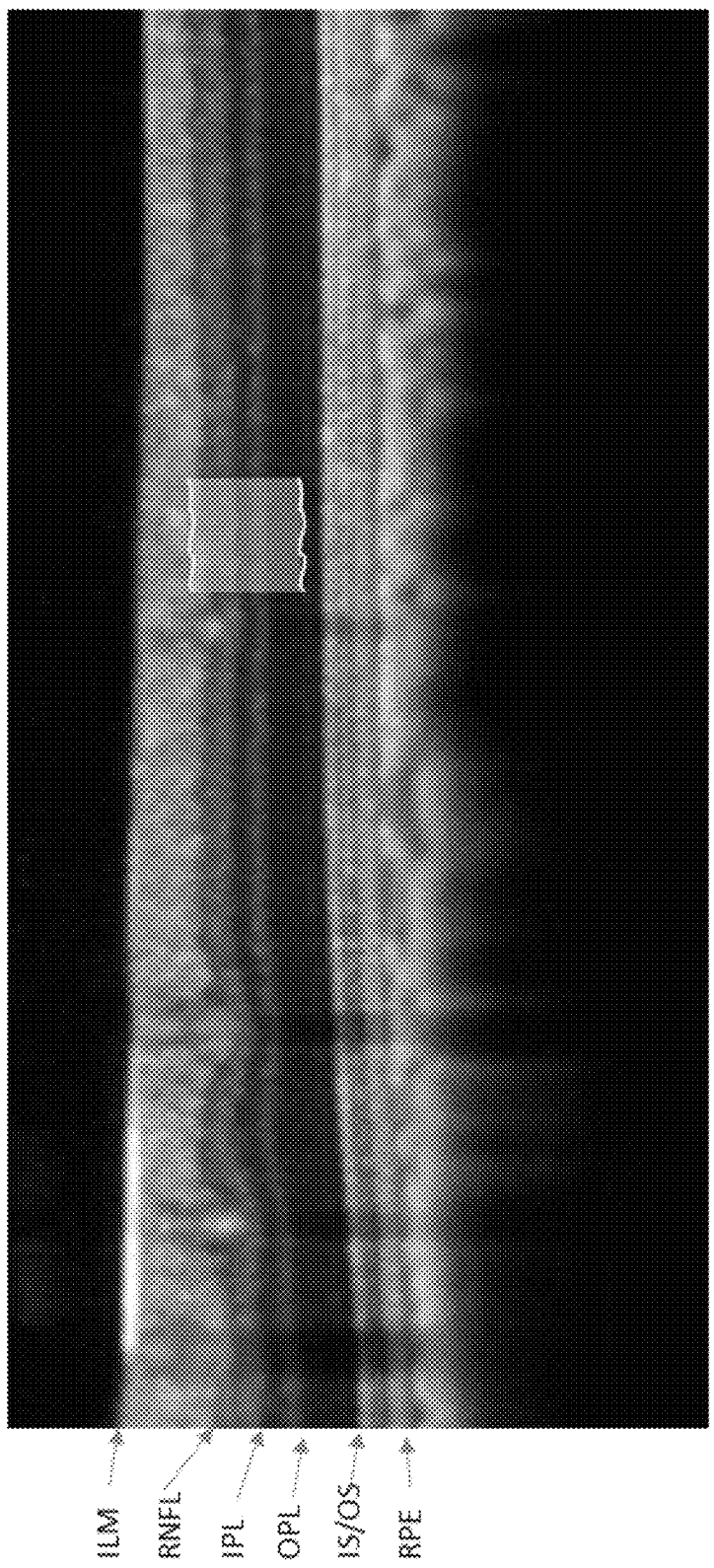
FIG. 3 is an OCT image of a retina where a surface of a portion of a retinal layer has been designated.

The systems, devices and processes of the present invention may be explained in relation to FIGS. 1 to 3. The block diagram of FIG. 1 showing a logic flow diagram is not intended to indicate that the process include all of the steps in every case. Moreover, any number of additional or alternative steps not shown in FIG. 1 may be included in the process, depending on the details of the specific implementation. This present invention provides a semi-automatic algorithm that does not require the prior knowledge of which surface to be segmented, and relies on the user to provide the initial input. This algorithm is particularly useful for retinal and/or choroidal OCT images because of the discretely flat-layered architecture of these structures. In some embodiments, a machine learning subroutine is performed to allow further automation, predictive modeling and development of algorithms for automated segmentation of OCT images and association of a disease state with the image and data contained therein.

Referring to FIG. 1, the process 100 of the present invention begins at block 105 where a 3D OCT dataset is obtained. As described above, the 3D OCT dataset is preferably an image of a patient retina obtained by scanning the patient's retina with an SD-OCT machine. FIG. 2 provides an exemplary patient OCT image of a retina showing multiple, well-structured retinal layers. Traditionally, computational segmentation algorithms were developed for each designated surface. These algorithms utilized image segmentation methods that do not require user inputs. However, these algorithms often fail due to the complexity of retinal structure in healthy and diseased eyes. In addition, if a user desired to segment a particular surface that no algorithm was developed in advance, the only option available will be to draw the designated surface manually. The manual process is usually laborious and inefficient.

In preferred embodiments, the OCT image is displayed on the display of a work station as described above. At block 110, a user at the work station determines the retinal layer to segment. At block 115, the user draws a small edge that corresponds to the designated retinal surface in order to begin the segmentation process. This user input associates the designated retinal segmentation surface (e.g., outer border of the inner plexiform layer) with the axial locations at a group of the adjacent A-scans. This is shown in the highlighted portion of FIG. 3. In some embodiments, the drawn edge covers a distance of from 5 to 100 columns of the image, preferably 10 to 50 columns of the image, and most preferably from about 20 to about 30 columns of the image. In preferred embodiments, the work station is configured with software to extract and average the intensity of each pixel for a designated distance above and below the drawn edge and the pixel intensity is averaged across the columns. In some embodiments, from about 5 to about 50 pixels above and below the drawn edge are averaged, and preferably from about 10 to about 30 pixels above and below the drawn edge are averaged, and most preferably about 20 pixels above and below the drawn edge are averaged. This process results in a local reflectivity profile of the designated surface and is depicted in block 120. In some embodiments, the axial "window" of the reflectivity profile may expand to cover the entire column, or to cover only a small area of interest either measured by pixels or measured by actual axial depth (in mm).

In one embodiment, the software is configured to utilize the local reflectivity profile and the user-determined location (extracted from the previous step) to segment the rest of the OCT dataset. As shown in block 125, the software is configured to utilize the local reflectivity profile to identify the potential pixel location of the designated retinal layer at each column across the OCT retinal image. This is achieved by finding the best fit of the reflectivity profile against each column. In preferred embodiments, the software associated with the user station is configured to utilize a cross-correlation operation or other best-fit algorithm to perform this operation. As shown in block 130, once the location of the pixels for the designated retinal layer are identified, the software is configured to run additional edge processing steps to finalize the segmentation of the retinal layer.

At any time during the processing of the retinal OCT image on the work station as shown in FIG. 1, the user may optionally tag the image or a portion of the image such a drawn edge or retinal layer with meta data. Examples of such tags include, but are not limited to, name of the surface, location at the retina, disease indication (e.g. age-related macular degeneration (AMD), diabetic retinopathy, uveitis, glaucoma, central vein occlusion, etc.), and lesion indication (geographic atrophy, retinal detachment, drusen, etc.).

In further embodiments, the processes of the present invention encompass building a machine learning database to provide predictive modeling of segmentation of retinal layers in a retinal OCT image. These processes are depicted in blocks 135, 140 and 145 of FIG. 1. In block 135, an OCT image and/or associated data such as the reflectivity profile and meta data tags are transmitted to a cloud server. In preferred embodiments, the cloud server comprises a database of OCT retinal images from both normal and diseased retinas as shown in block 140. In preferred embodiments, machine learning algorithms are applied to generate prediction algorithms for the automatic segmentation of OCT images, especially those related to diseased retinas. In some embodiments, additional inputs are provided at this stage of the process. These inputs include, but are not limited to, expert input as to the exact placement of the segmentation line correlating to specific morphological components of the vitreous, retina and/or choroid and parameter-based stratification of the segmentation (as in each disease condition, the reflectivity profile may change shape due to disease process). In some embodiments, the algorithms utilize the reflectivity profiles to automatically identify lesions in one or more of the retinal layers. It will be understood that "lesions" refers to alterations in the retinal structure that are identified in images of diseased retinas but not present in images of normal retinas. The algorithms may further provide automated disease diagnosis and/or severity staging based on data associated with the lesion, for example, the reflectivity profile associated with the lesion, the size of the lesion, the location of the lesion on the retina, and/or the location of the lesion within one or more retinal layers.

In some embodiments, the work station and/or cloud server include an image server. The image server may include an information storage unit for short-term storage of images generated by the OCT imaging devices. In addition, the image server may include an archival storage unit, e.g., an optical disc storage and optical disc reader system, for long-term storage of images generated by the imaging devices. Furthermore, the image server may be configured to retrieve any of the images stored in the information storage unit and/or the archival storage unit, and send such images to any of the workstations or cloud server to be analyzed according to the embodiments described herein.

The present invention contemplates that a variety of machine learning algorithms may be applied to the OCT image data. Example data mining techniques include factor analysis, principal component analysis, correlation analysis, etc. as understood by a person of skill in the art. As a non-limiting example of suitable software, SAS™ Enterprise Miner™ includes nodes for exploring data and selecting or modifying control variables as input variables. Examples nodes include transformation nodes, clustering nodes, association rule nodes, a variable selection node, a descriptive statistics node, a principal components node, etc. The software can further include multiple types of objective function models for neural networks (AutoNeural, DMNeural, Neural Network), decision trees (Decision Tree, Gradient Boosting), regression models (Dmine Regression, Least Angle Regressions (LARS), Regression), k-nearest neighbors models (Memory Based Reasoning (MBR)), a partial least squares model (Partial Least Squares), a support vector machine (Support Vector Machine), an ensemble of models that are integrated to define an objective function model (Ensemble), etc. In some preferred embodiments, the software includes neural network procedures that can be used to configure, initialize, train, predict, and score a neural network model.

In some preferred embodiments, the machine learning analysis provides models and/or algorithms for automated segmenting of retinal layers in an OCT image. In these embodiments, when a surface segmentation is called, an algorithm developed by the machine learning process and optionally utilizing a corresponding group of reflectivity profiles saved in the cloud database is used to generate a disease-specific segmentation result. These results may then be transmitted to a work station or to a health care provider. In some further embodiments, software resident at work stations associated with OCT imaging devices may be updated with algorithms or models developed by the machine learning process so that segmentation and disease calls may be automated at the individual work station level.

In some embodiments, the processes, work stations, and systems described above are configured and utilized to monitor changes in a given patient's retinal images over time. In some embodiments, processors associated with either the work stations or cloud served include software on a non-transitory computer readable medium to automatically compare two or more patient retinal images for a given patient that are obtained over a given period of time. For example, the images may be obtained at 1 day, 2 day, 3 day, 4 day, 5 day, 1 week, 2 week, 3, week. 4 week, 1 month, 2 month, 3 month, 4 month, 5 month, 6 month, 1 year, 2 year, 3 year, 4 year of five year intervals, or for an internal with these specifically identified periods. Accordingly, in some embodiments, the process comprise obtaining multiple (i.e., two or more) patient retinal images over a defined time period for a given patient, via a processor automatically analyzing the multiple retinal images to identify changes in the retinal images, and displaying an image showing the identified changes in the patient retinal images. These processes find particular use in clinical settings, for example, where a patient is being monitored for disease progression of for response to a particular therapy or therapeutic agent. The processes may also be used to monitor patients participating in a clinical trial. Accordingly, in some embodiments, the processes of the present invention comprise obtaining multiple patient retinal images over a defined period of time and analyzing the images to monitor disease progression over time. In further embodiments, the processes of the present invention comprise treating a patient with a therapy or therapeutic agent and then obtaining multiple retinal images for the patient over a given period of time to monitor the response of the patient to the therapy or therapeutic agent. The therapy or therapeutic agent may be approved by the Federal Drug Administration (FDA) or may be undergoing a clinical trial for approval. In some embodiments, the therapeutic agent is selected from the group consisting of a small molecule drug, a biologic drug, a nucleic acid, and a cell. In some embodiments, the therapeutic agent is delivered to the patient by a method selected from the group consisting of topical application to the surface of the eye, subconjunctival injection, systemically (IV, oral, subcutaneous, intramuscular), electrophoresis, intravitreal injection, subretinal delivery, and suprachoroidal delivery. In some embodiments, the therapeutic agent is soluble, insoluble in a suspension, of incorporated into a biomaterial platform.

It will be appreciated that the invention also applies to computer programs, particularly computer programs on or in a carrier, adapted to put the invention into practice. The program may be in the form of a source code, an object code, a code intermediate source and object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a floppy disc or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

It should be noted that the above-mentioned embodiments have its application beyond the retina imaging. In the field of ophthalmology, it is applicable to be used directly in in the eye for cornea to delineate tear film, epithelium, Bowman's layer, stroma, Descemet's membrane, endothelium and retrocorneal disease processes exemplified by but not limited to retrocorneal membranes. Additionally, it applies to other fields utilizing OCT technology to delineate laminated boundries within a structure both biologic and nonbiologic. Examples where OCT is used in medicine include but are not limited to assessment of the cornea and tear film, the gastrointestinal tract (Tsai, Tsung-Han, James G. Fujimoto, and Hiroshi Mashimo. "Endoscopic optical coherence tomography for clinical gastroenterology." diagnostics 4, no. 2 (2014): 57-93.), Dentistry (Otis, L. L., Everett, M. J., Sathyam, U. S. and COLSTON, B. W., 2000. Optical coherence tomography: A new imaging: Technology for dentistry. The Journal of the American Dental Association, 131(4), pp. 511-514.), Respiratory (D'Hooghe, J. N. S., De Bruin, D. M., Wijmans, L., Annema, J. T. and Bonta, P. I., 2015. Bronchial wall thickness assessed by optical coherence tomography (OCT) before and after bronchial thermoplasty (BT). European Respiratory Journal, 46(suppl 59), p. OA1763.), other medical fields, and monitoring of biointegration of implanted biomaterials.

What is claimed is:

1. An optical coherence tomography (OCT) image analysis process comprising:
   visualizing an OCT dataset from a scan of a patients retina on a display device, wherein the image displays a plurality of cross-sectional retinal layers of the retina;
   indicating a portion of an edge of at least one of the retinal layers with a user input device to provide a designated retinal layer;
   at a user work station, calculating a patient reflectivity profile for the designated retinal layer and using the reflectivity profile to identify potential retinal locations of the designated retinal layer across the entire image;
   transmitting the patient reflectivity profile to a server remote from the user work station, wherein the remote server comprises a plurality of OCT datasets from normal and diseased retinas;
   via a processor associated with the remote server, applying one or more machine learning algorithms to analyze the patient reflectivity profile in relation to the plurality of OCT datasets from normal and diseased retinas to generate one or more algorithms that automatically segment retinal layers in an OCT image, automatically identify lesions in one or more retinal layers, and/or associate a disease with an automated segmentation or lesion identification result,
   wherein the algorithm facilitates displaying a refined trace of the designated retinal layer.

2. The process of claim 1, further comprising the step of displaying an image with a refined trace of the designated retinal layer generated by the algorithm.

3. The process of claim 2, further comprising the step of transmitting the image with a refined trace of the designated retinal layer to a user.

4. The process of claim 1, wherein the algorithm associates the reflectivity profile of the designated retinal layer with a disease state of the retina wherein the disease state is selected from the group consisting of Age-related macular degeneration, diabetic retinopathy, retinitis pigmentosa, uveitis, central vein occlusion, and other retinal degenerations.

5. The process of claim 4, further comprising the step of using the algorithm to associate a disease state or normal state with the patient retina.

6. The process of claim 1, wherein the algorithm identifies lesions in one or more retinal layers.

7. The process of claim 6, wherein the type and/or location of the lesion is used to diagnose a disease or the retina and/or designate a stage of severity of a disease of the retina.

8. The process of claim 5, further comprising transmitting information about the disease state or normal state of the patient retina to a user.

9. The process of claim 7, further comprising transmitting information about the lesion, disease associated with the lesion, or stage of severity of retinal disease to a user.

10. The process of claim 1, further comprising the step of tagging the patient reflectivity profile with an information identification tag, wherein the information identification tag comprises information selected from the group consisting of name of the surface, location at the retina, disease indication and lesion indication, retinal location relating to known retinal landmark (e.g., fovea), age, gender, race, and animal species (other than human).

11. The process of claim 1, wherein the display device is networked with an SD-OCT device.

12. The process of claim 11, wherein the process further comprising the step of utilizing the SD-OCT device to obtain the OCT dataset of the scan of the patient's retina.

13. The process of claim 1, wherein the server remote from the user work station is a cloud based server.

14. The process of claim 1, wherein the one or more machine learning algorithms are selected from the group exemplified by but not limited to a neural network, a decision tree, a regression model, a k-nearest neighbor model, a partial least squares model, a support vector machine and an ensemble of the models that are integrated to define an algorithm.

15. The process of claim 1, further comprising obtaining multiple patient retinal images over a defined time period for a given patient, via a processor automatically analyzing the multiple retinal images to identify changes in the retinal images, and displaying an image showing the identified changes in the patient retinal images.

* * * * *